United States Patent
Yang et al.

(10) Patent No.: US 9,952,152 B2
(45) Date of Patent: Apr. 24, 2018

(54) OPTIC DISTRIBUTION METER

(71) Applicant: National Central University, Taoyuan (TW)

(72) Inventors: Tsung-Hsun Yang, Taoyuan (TW); Ching-Cherng Sun, Taoyuan (TW); Yeh-Wei Yu, Taoyuan (TW); Chao-Chuan Chen, Taoyuan (TW)

(73) Assignee: NATIONAL CENTRAL UNIVERSITY, Taoyuan (TW)

( * ) Notice: Subject to any disclaimer, the term of this patent is extended or adjusted under 35 U.S.C. 154(b) by 260 days.

(21) Appl. No.: 15/014,144

(22) Filed: Feb. 3, 2016

(65) Prior Publication Data
US 2017/0067824 A1    Mar. 9, 2017

(30) Foreign Application Priority Data
Sep. 9, 2015 (TW) .............................. 104129831 A

(51) Int. Cl.
*G01N 21/47* (2006.01)
*G01N 21/55* (2014.01)

(52) U.S. Cl.
CPC ....... *G01N 21/55* (2013.01); *G01N 2021/555* (2013.01)

(58) Field of Classification Search
CPC .. G01N 2021/555; G01N 21/55; G01N 21/17; G01J 1/0271
See application file for complete search history.

(56) References Cited

U.S. PATENT DOCUMENTS

| 5,241,369 A * | 8/1993 | McNeil ................ G01B 11/303 356/445 |
| 9,625,309 B2 * | 4/2017 | Baboulaz ............... G01N 21/55 |
| 2016/0161330 A1 * | 6/2016 | Baboulaz ............... G01N 21/55 356/445 |

* cited by examiner

*Primary Examiner* — Nathnael Aynalem
(74) *Attorney, Agent, or Firm* — Juan Carlos A Marquez; Marquez IP Law Office, PLLC

(57) ABSTRACT

The present invention discloses an optic distribution meter that includes a testing system and an imaging system. The testing system includes an arc-shaped brace which has an extended object holder; and a rail base which has a first rail. The imaging system, set at a side of the testing system, includes a screen and an image catcher. With the implementation of the present invention, the rail base is able to rotate or move an object to a test angle with very little light blocking of measurements. Besides, with the first rail supporting the object, the incident angle of the light of a light source to the object remains unchanged when the measuring angle of the imaging system is changed. Thus ensure the accuracy of measurements of the optic distribution meter.

12 Claims, 9 Drawing Sheets

OPTIC DISTRIBUTION METER

BACKGROUND OF THE INVENTION

1. Technical Field

The present invention relates to an optic distribution meter and more particularly to an optic distribution meter which includes a first rail.

2. Description of Related Art

When object is illuminated by a light, the light will be refracted, reflected, absorbed or scattered by the object. Objects with different material or surface characteristics generate different scattering characteristics. The scattering characteristics of an object is normally represented by BSDF (bi-directional scattering distribution function) of the object, with BSDF being a function of a light incident angle and the light scattering angle.

That is, BSDF is a measuring of the scattering of an object, and is widely applied to optics related industries such as textile, cosmetics, panting, illumination, 3D computer graphics and displays.

Actual applications of the scattering of objects requires a measuring equipment to measure the scattering signals with respect to different measuring angles together with a data processing equipment to generate accessible data. For instance, module performance of a reflecting sheet, a light guiding panel, a diffusion film or a bright enhanced film depends very much on the scattering performance, getting detail information about the scattering performance or BSDF of them helps big deal in optimizing the parameters in production or applications.

However, developments of most of the scattering signal measurement equipment nowadays focus only on the performance improvements of dynamic range, sensitivity or low noise. The measurements of the scattering signals of object still suffer from unwanted light blocking or error deviation of incident light to object that degrades enormously the accuracy of measurement.

In view of the above, it is an important issue for the optics or the material industry or even the research and development activities of them to overcome the aforesaid drawbacks of the conventional scattering signal measurement equipment and to provide a measurement structure of an optic distribution meter which meets the requirements of neither blocking of incident light to object when changing the measuring angle, nor error deviation when changing the incident angle of the light, which therefore contributes to enhancing the quality and accuracy of measurements. To this end, it is most desirable that a highly efficient optic distribution meter, or more particularly an optic distribution meter with a rail, can be made by forming a first rail on the testing system of the optic distribution meter.

BRIEF SUMMARY OF THE INVENTION

The present invention relates to an optic distribution meter that includes a testing system and an imaging system. The testing system includes an arc-shaped brace which has an extended object holder; and a rail base which has a first rail. The imaging system, set at a side of the testing system, includes a screen and an image catcher. With the implementation of the present invention, the rail base is able to rotate or move an object to a test angle with very little light blocking of measurements. Besides, with the first rail supporting the object, the incident angle of the light of a light source to the object remains unchanged when the measuring angle of the imaging system is changed. Thus ensure the accuracy of measurements of the optic distribution meter.

More specifically, the present invention provides an optic distribution meter, comprising: a testing system, which includes: an arc-shaped brace, which includes an object holder extended from a base point on the said arc-shaped brace, the said object holder is used to hold an object; and a rail base, which connects to and supports the arc-shaped brace, the rail base includes a first rail implanted on top of the rail base, a first motor and a second motor connected to the rail base, wherein the first motor controls the rail base to rotate with respect to a first axis, the second motor controls the arc-shaped brace to move along the first rail, and wherein the first axis is the central axis of the rail base; and an imaging system that equipped on a side of the object holder, the imaging system includes: a screen, the optic distribution information scattered from the object is projected to and displayed on a surface of the screen; and an image catcher, which is implemented on a side of the screen to catch and record the optic distribution information displayed on the said surface of the screen.

Implementation of the present invention at least produces the following advantageous effects:

1. The testing system can rotate or move to every angles of observation with minimal blocking of light.

2. With the first rail supporting the testing system, the incident angle of the light source toward the object can be obtained when changes of the angle of observation is required, to ensure the measuring accuracy of the optic distribution information scattered from the object.

The features and advantages of the present invention are detailed hereinafter with reference to the preferred embodiments. The detailed description is intended to enable a person skilled in the art to gain insight into the technical contents disclosed herein and implement the present invention accordingly. In particular, a person skilled in the art can easily understand the objects and advantages of the present invention by referring to the disclosure of the specification, the claims, and the accompanying drawings.

BRIEF DESCRIPTION OF THE SEVERAL VIEWS OF THE DRAWINGS

The invention as well as a preferred mode of use, further objectives and advantages thereof will be best understood by reference to the following detailed description of illustrative embodiments when react in conjunction with the accompanying drawings, wherein.

DETAILED DESCRIPTION OF THE INVENTION

Figure 1:
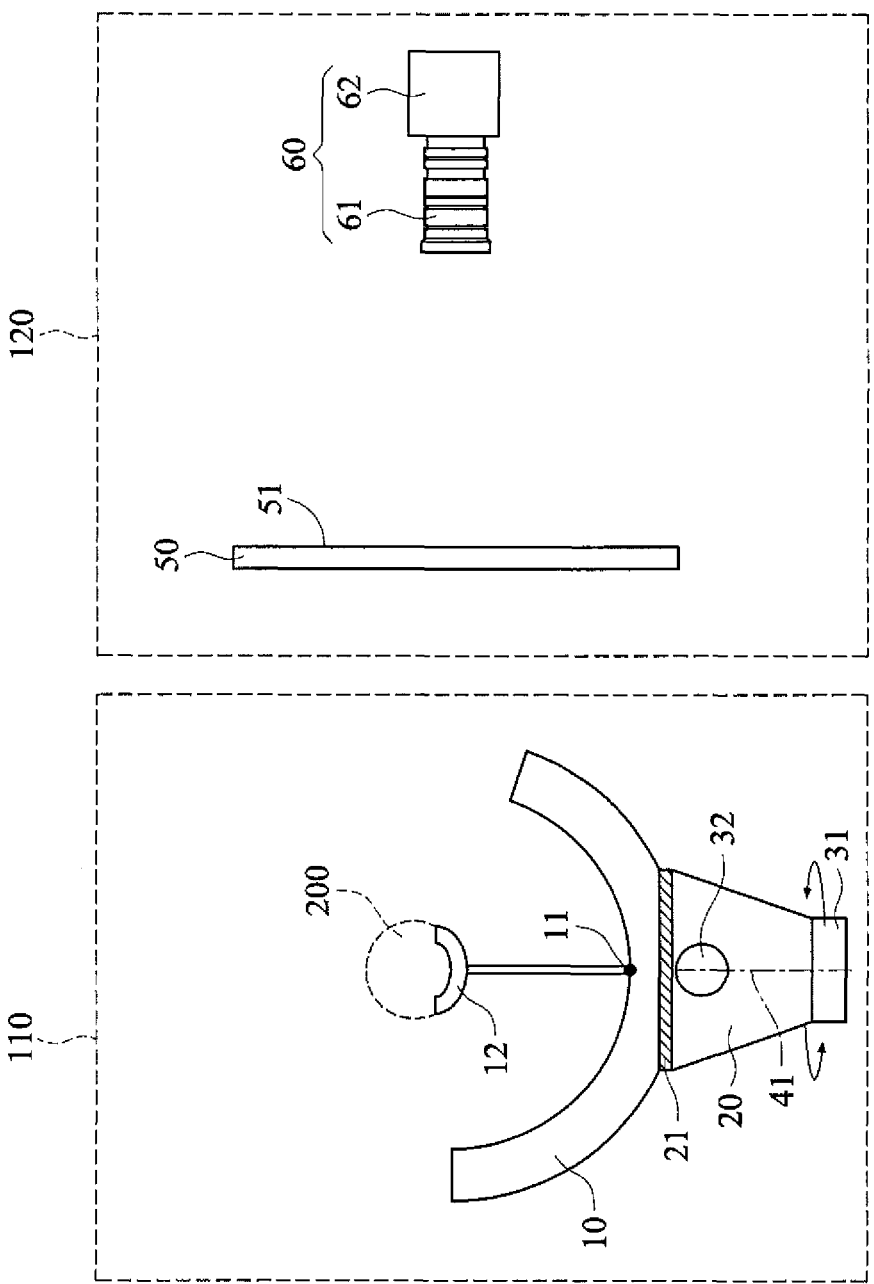
FIG. 1 is a schematic system view of the optic distribution meter according to an embodiment of the present invention.

Please Refer to FIG. 1, the optic distribution meter 100 in an embodiment of the present invention comprises a testing system 110 and an imaging system 120. The testing system 110 includes an arc-shaped brace 10 and a rail base 20, while the imaging system 120 includes a screen 50 and an image catcher 60.

As shown in FIG. 1, the arc-shaped brace 10 has a base point 11 and an object holder 12 located extending from the base point 11 toward the center of the arc of the arc-shaped brace 10. There is no specific limitation on the length or height of the object holder 12 as long as the object holder 12 holds the object 200 to be tested well, however, the better location of the object holder 12 is to locate as close to the center of the are of the arc-shaped brace 10 as possible.

As shown in FIG. 1, the rail base 20 connects to and supports the arc-shaped brace 10, the rail base 20 includes a first rail 21 implanted on top of the rail base 20, a first motor 31 and a second motor 32 connected to the rail base 20, wherein the first motor 31 controls the rail base 20 to rotate with respect to a first axis 41, the second motor 32 controls the arc-shaped brace 10 to move along the first rail 21, and wherein the first axis 41 is the central axis of the rail base 20.

As also shown in FIG. 1, the imaging system 120 which equipped on a side of the object holder 12 includes a screen 50 and an image catcher 60. The optic distribution information scattered from the object 200 is projected to and displayed on a surface 51 of the screen 50. Wherein, when the object 200 is an object 200 that emits light, no illumination source of any kind is required to illuminate the object 200, and there will still be optic distribution information displayed on a surface 51 of the screen 50.

Figure 6A:
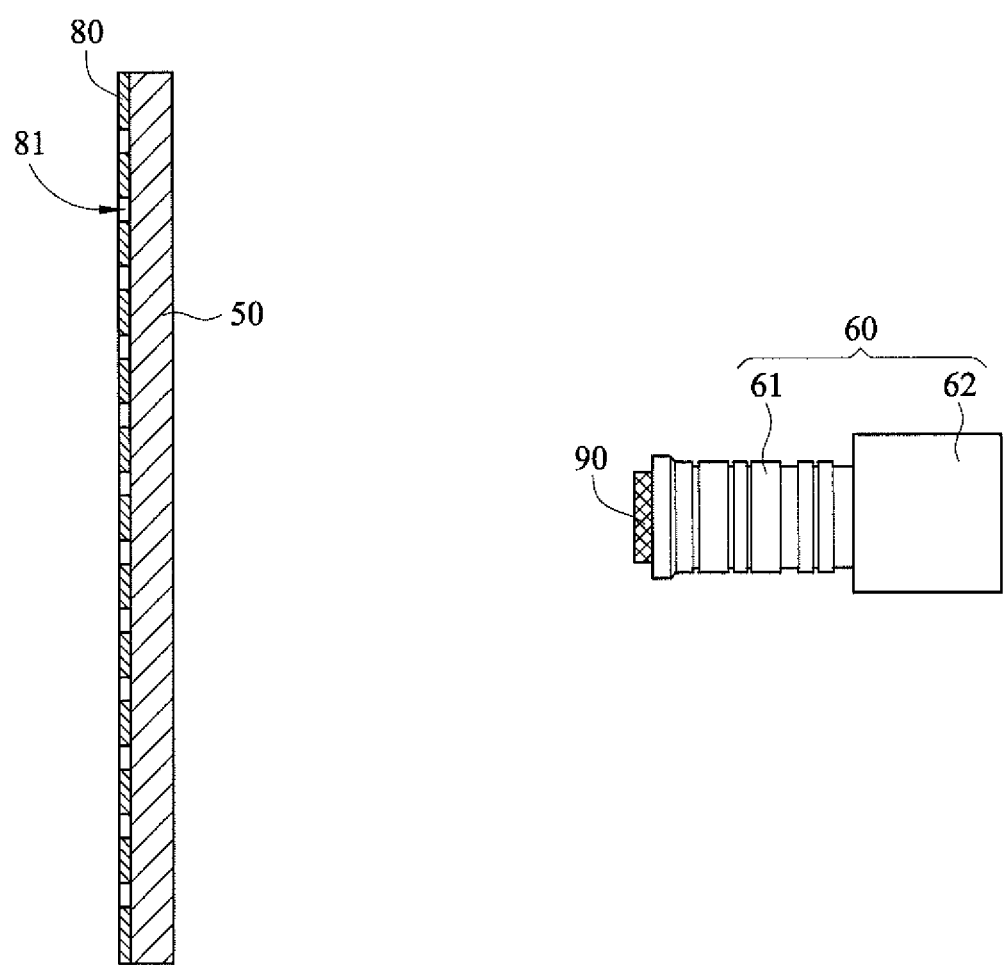
FIG. 6A is a schematic view of a grating is implemented in between the screen and the image catcher according to an embodiment of the present invention.
Figure 6B:
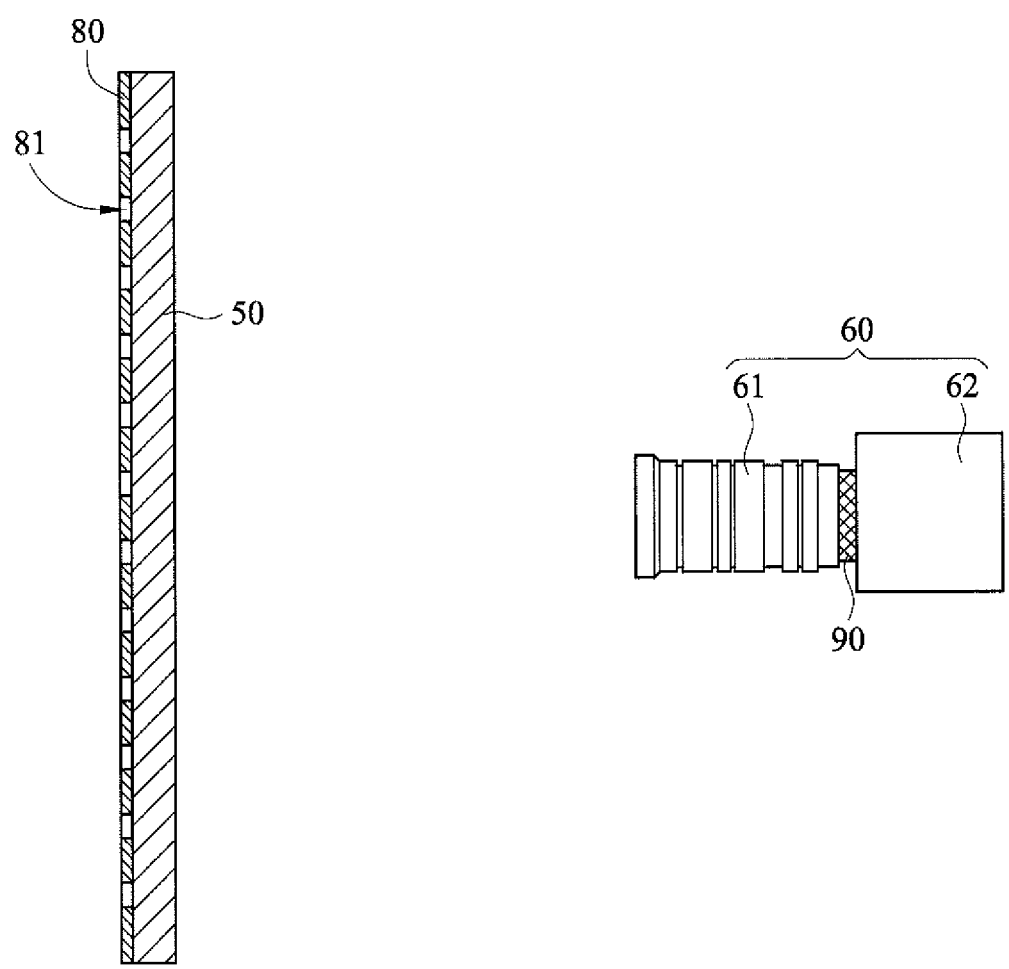
FIG. 6B is a schematic view of a grating is implemented in between the lens unit and the image catcher according to an embodiment of the present invention.

With continued reference to FIG. 1, FIG. 6A and FIG. 6B, the image catcher 60 is implemented on a side of the screen 50 to catch and record the optic distribution information scattered from the object 200 and displayed on the said surface 51 of the screen 50. The image catcher 60 can be a lens unit 61 integrated together with an image detector 62, or the image catcher 60 can be a camera, a camcorder or any other image catching device.

Figure 2:
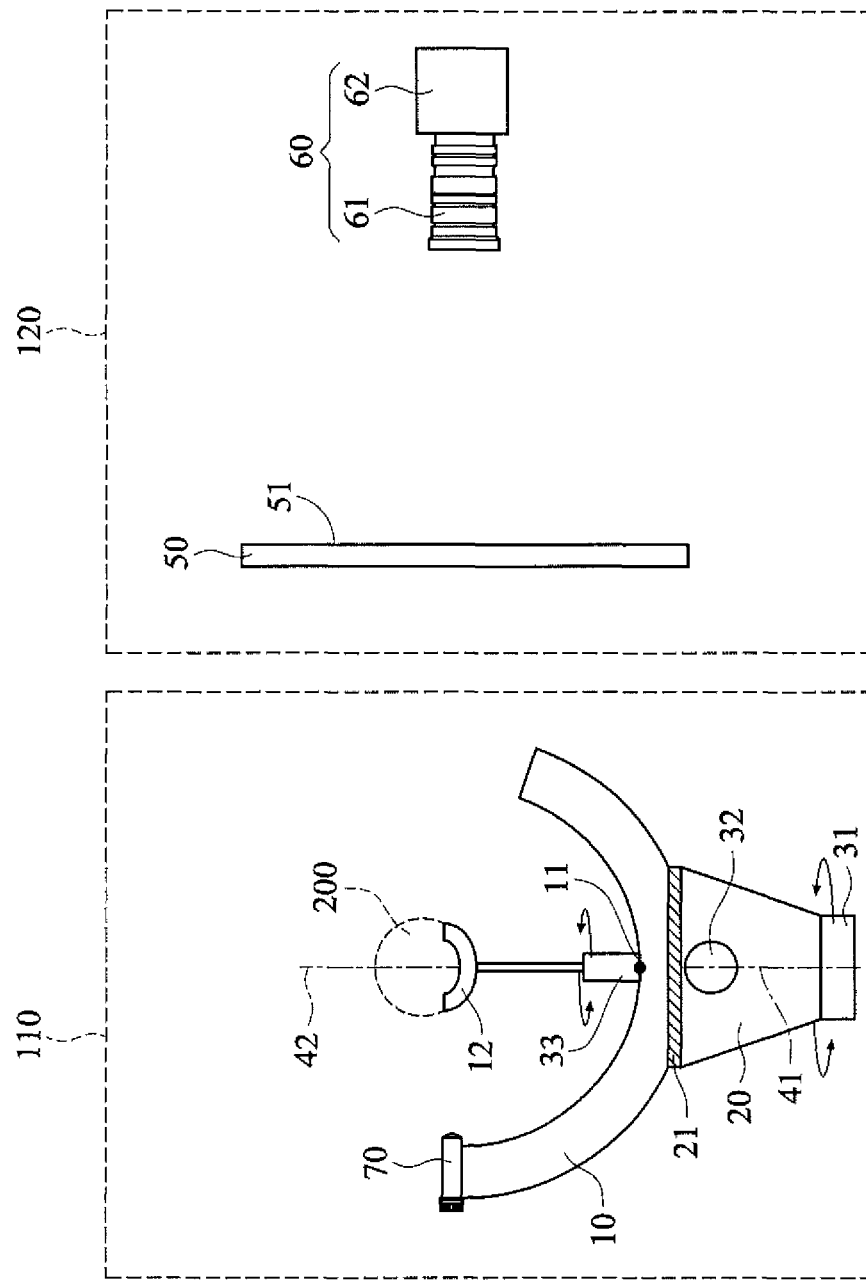
FIG. 2 is a schematic system view of the optic distribution meter further includes a third motor according to an embodiment of the present invention.

As shown in FIG. 2, the testing system 110 may further includes a third motor 33. The third motor 33 is implemented on the base point 11 of the object holder 12, wherein the said third motor 33 controls the object holder 12 to rotate with respect to a second axis 42.

Figure 3:
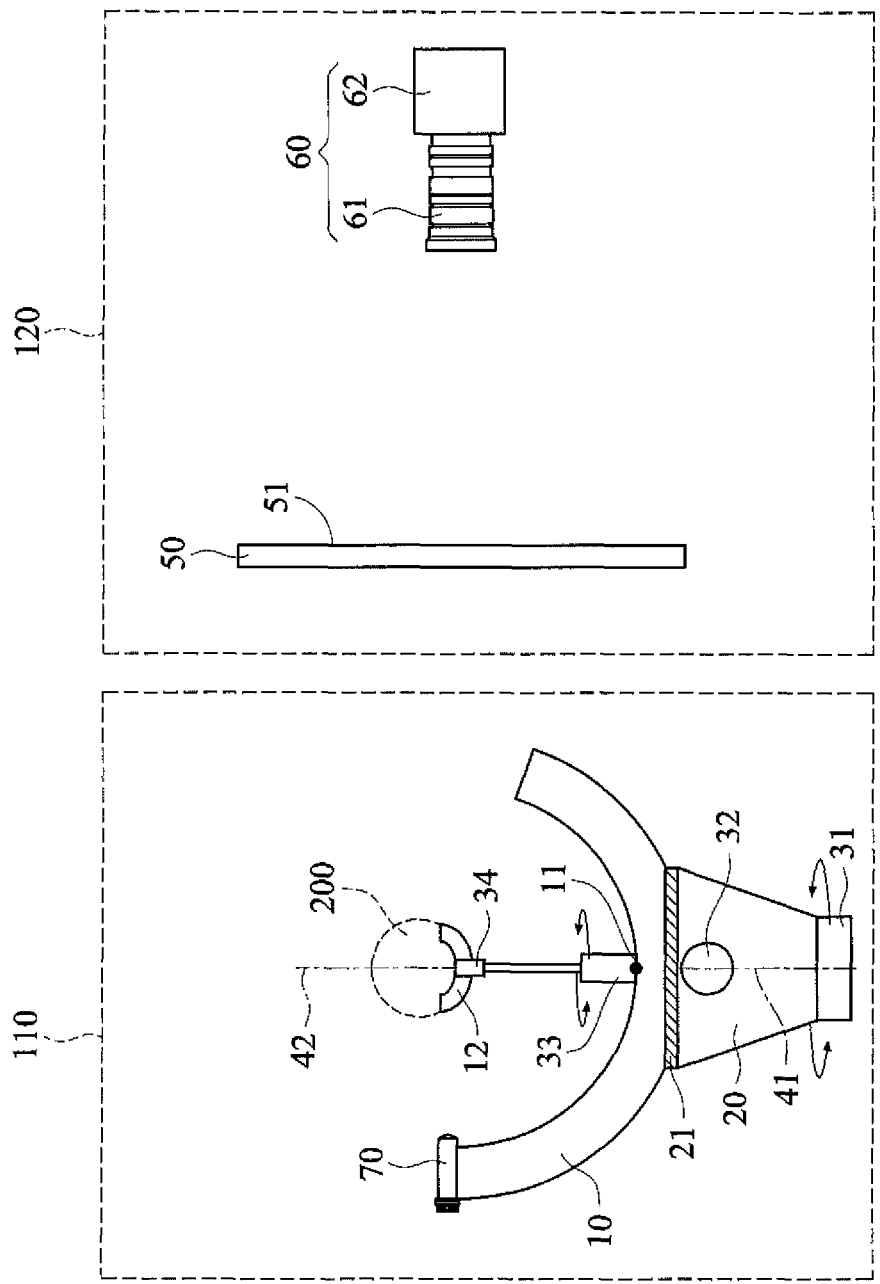
FIG. 3 is a schematic system view of the optic distribution meter further includes a third motor and a fourth motor according to an embodiment of the present invention.

Referring to FIG. 3, the testing system 110 that includes the third motor 33 may further includes a fourth motor 34. The fourth motor 34 is connected to the object holder 12 and controls the object 200 to spin along the object holder 12, wherein the object holder 12 can also be another rail and the fourth motor 34 controls the object 200 to spin along this rail.

Figure 4:
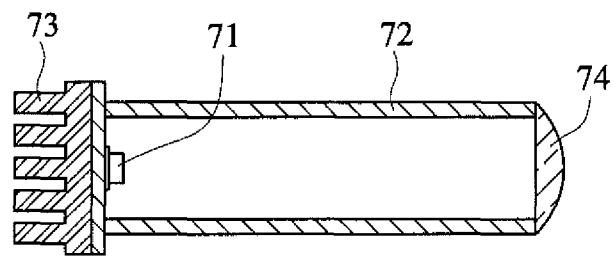
FIG. 4 schematically shows the light source according to an embodiment of the present invention.

With reference to FIG. 2, FIG, 3 and FIG. 4, the testing system 110 can further includes a light source 70 fixed or located on one end of the arc-shaped brace 10, wherein the light source 70 is an illumination module which includes at least one light emitting object 71, a light guiding tube 72, a heat sink 73 and a converging lens 74.

As shown in FIG. 3, the second axis 42 which the said third motor 33 controls the object holder 12 to rotate with respect to, in the meantime, is the line extended from the center point of the illumination spot on the surface of the object 200 projected from the light source 70 toward the object 200 to the base point 11.

Figure 7:
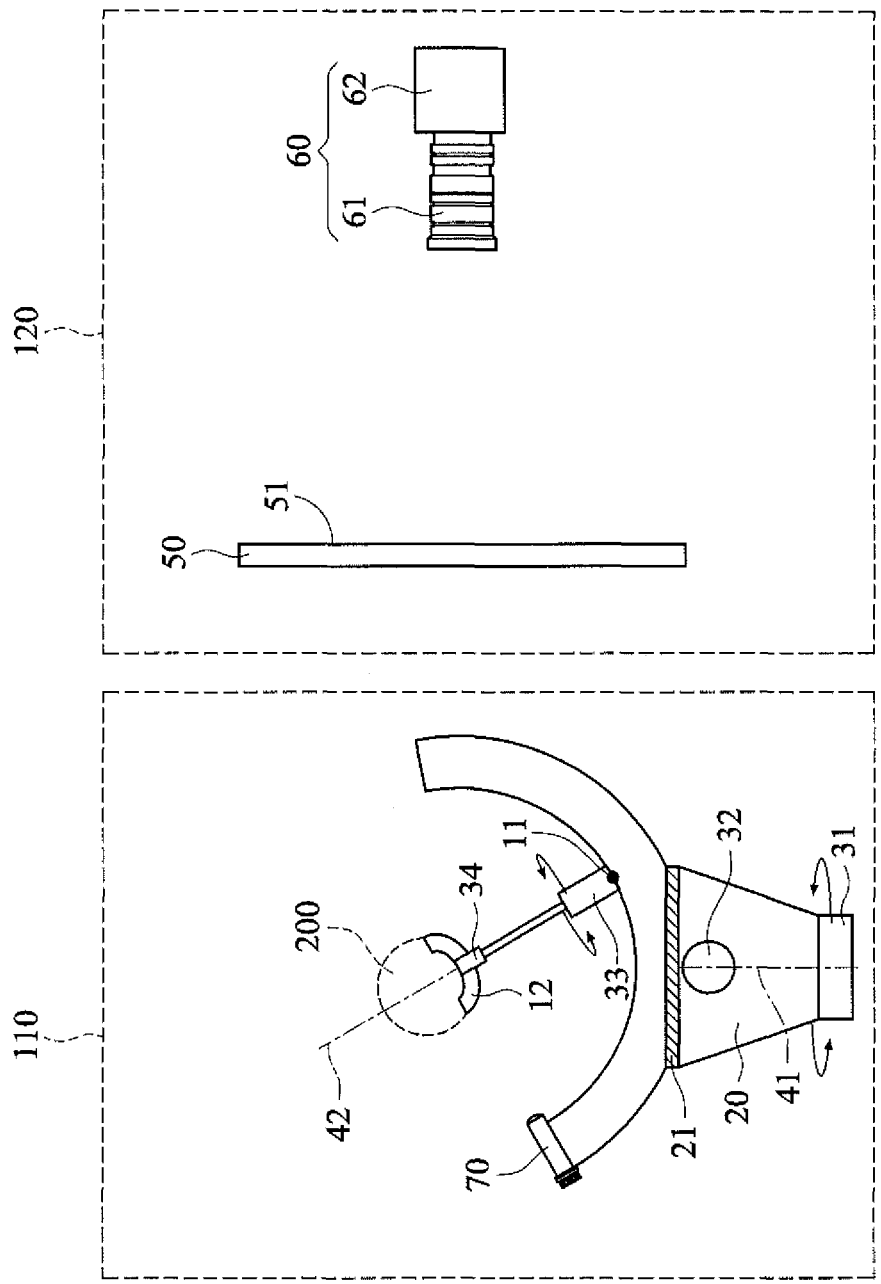
FIG. 7 schematically shows the arc-shaped brace and the object holder move on the rail base according to an embodiment of the present invention.

As shown in FIG. 2, FIG. 3 and FIG. 7, when the object 200 does not emit light, the light source 70 is required to illuminate the object 200 to obtain the optic distribution information scattered from the object 200 and displayed on the said surface 51 of the screen 50.

Referring back to FIG. 4, the converging lens 74 forms a magnified image of the light emitting object 71 and projects it toward the object 200, wherein the magnifying ratio of the converging lens is between 2 to 20, wherein the converging lens 74 can be a plano-convex lens or a convex lens.

The range of the projection of the magnified image of the light emitting object 71 toward the object 200 can be from 5 mm in the front of the center of object 200 to 5 mm in the back of the center of object 200 in a straight line connected from the center of the converging lens 74 to the center of the object 200.

The light guiding tube 72 as shown in FIG. 4 may be a light guiding tube 72 with a sidewall to block the light emitted by the light emitting object 71 toward the sidewall, wherein the absorption ratio of light of the sidewall is no less than 90%. The effect is to reduce the emitting maximum span angle of the light emitted from the light source 70 and make efficient the usage of the light source 70.

Figure 5A:
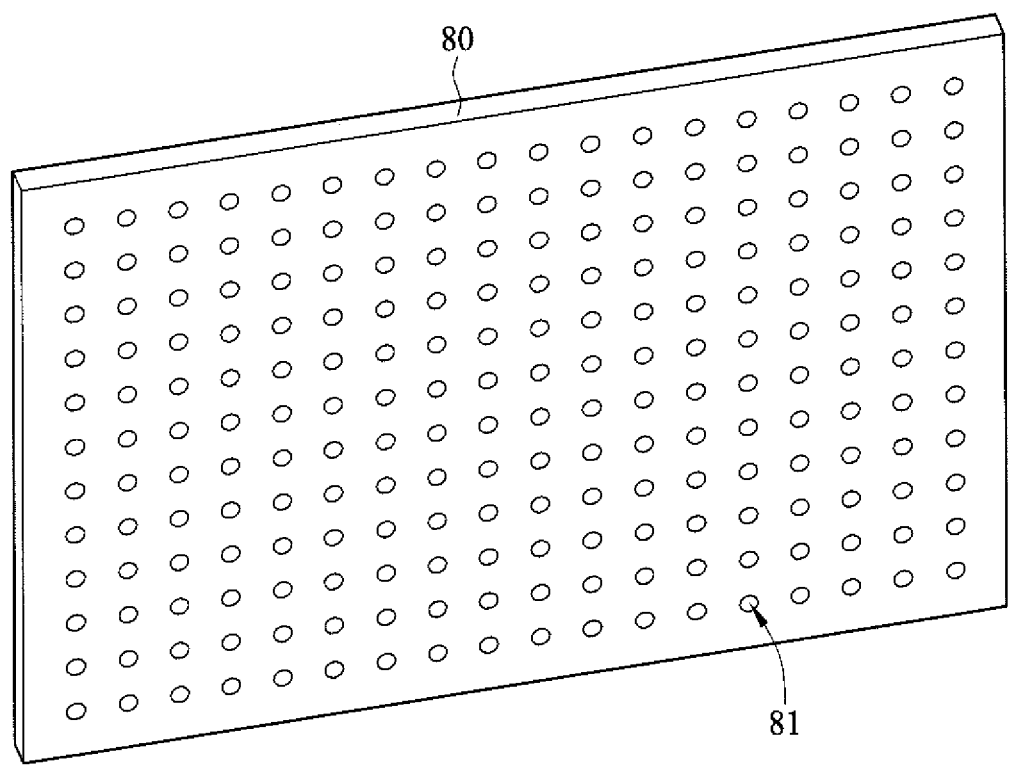
FIG. 5A is a schematic view of the light shielding layer with plural penetrating holes in a 2-dimensional distribution according to an embodiment of the present invention.
Figure 5B:
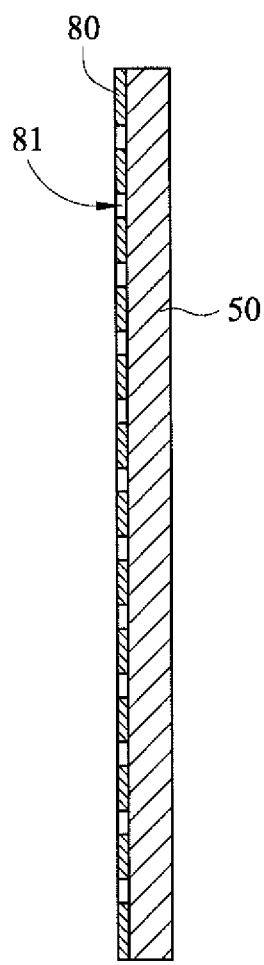
FIG. 5B is a schematic view of the light shielding layer with plural penetrating holes in a 2-dimensional distribution attached to the screen according to an embodiment of the present invention.

Referring to FIG. 5A and FIG. 5B, with the implementation of a light shielding layer 80 attached to the screen 50, wherein the light shielding layer 80 comprises plural penetrating holes 81 in a 2-dimensional distribution, 2-dimensional optic distribution information scattered from the object 200 can directly be obtained without having to adopt signal processing.

Referring now to FIG. 6A and FIG. 6B, the optic distribution meter 100 may further include a grating 90 implemented in between the screen 50 and the image catcher 60. With the implementation of the grating 90, the optic distribution information scattered from the object 200 is divided according to different optical or spatial frequencies before entering the image detector 62 of the image catcher 60.

As also shown in FIG. 6A and FIG. 6B, the grating 90 can be implanted in between the screen 50 and the image catcher 60, or the grating 90 can be implemented in between the lens unit 61 and the image detector 62.

All in all, as shown in FIG. 7, with the implementation of the first rail 21 or the implementation of both the first rail 21 and the object holder 12, the testing system 110 can be rotated or moved to an observation angle required with minimal blocking of light incident to the object 200. And with the first rail 21 supporting the testing system 110, the incident angle of the light source 70 toward the object 200 can be obtained when changes of the angle of observation is required, to ensure the measuring accuracy of the optic distribution information scattered from the object 200.

Otherwise, when the object 200 is a light emitting object 200, the illumination by the light source 70 is no longer required, wherein only the first motor 31 and the second motor 32 are needed to cover all the observation angles for optic distribution information scattered from the object 200.

On the other hand, when the object 200 is not a light emitting object 200 but is a symmetrically scattering object 200 that has uniform scattering in every directions, then only the third motor 33 is needed to work together with the first motor 31 and the second motor 32 to obtain all optic distribution information scattered in every observation angles. That is to say, the fourth motor 34 can be omitted when the object 200 is a symmetrically scattering object 200, such as a symmetrical ball shaped object 200.

The embodiments described above are intended only to demonstrate the technical concept and features of the present invention so as to enable a person skilled in the art to understand and implement the contents disclosed herein. It is understood that the disclosed embodiments are not to limit the scope of the present invention, Therefore, all equivalent changes or modifications based on the concept of the present invention should be encompassed by the appended claims.

What is claimed is:

1. An optic distribution meter, comprising:
   a testing system, which includes:
      an arc-shaped brace, which includes an object holder extended from a base point on the said arc-shaped brace, the said object holder is used to hold an object; and
      a rail base, which connects to and supports the arc-shaped brace, the rail base includes a first rail implanted on top of the rail base, a first motor and a second motor connected to the rail base, wherein the first motor controls the rail base to rotate with respect to a first axis, the second motor controls the arc-shaped brace to move along the first rail, and wherein the first axis is the central axis of the rail base; and
   an imaging system that equipped on a side of the object holder, the imaging system includes:
      a screen, the optic distribution information scattered from the object is projected to and displayed on a surface of the screen; and
      an image catcher, which is implemented on a side of the screen to catch and record the optic distribution information displayed on the said surface of the screen.

2. The optic distribution meter of claim I, wherein the said image catcher includes a lens unit and an image detector.

3. The optic distribution meter of claim 1, wherein the said testing system further includes a third motor implemented on the base point of the object holder, wherein the said third motor controls the object holder to rotate with respect to a second axis.

4. The optic distribution meter of claim 3, wherein the object holder is an object holding rail.

5. The optic distribution meter of claim 4, wherein the said testing system further includes a fourth motor connected to the object holder and controls the object to spin along the object holder.

6. The optic distribution meter of claim 2, wherein the testing system further includes a light source fixed on one end of the arc-shaped brace, wherein the light source is an illumination module which includes at least one light emitting object, a light guiding tube, a heat sink and a converging lens.

7. The optic distribution meter of claim 3, wherein the second axis is a line extended from the center point of the illumination spot on the surface of the object projected from the light source toward the object to the base point.

8. The optic distribution meter of claim 6, wherein the converging lens forms a magnified image of the light emitting object, wherein the magnifying ratio of the converging lens is between 2 to 20.

9. The optic distribution meter of claim 6, wherein the light absorption ratio of the sidewall of the light guiding tube is no less than 90%.

10. The optic distribution meter of claim 1, wherein a light shielding layer is attached to the said screen, wherein the light shielding layer comprises plural penetrating holes in a 2-dimensional distribution.

11. The optic distribution meter of claim 1, further comprises a grating, wherein the grating is implemented in between the screen and the image catcher.

12. The optic distribution meter of claim 2, further comprises a grating, wherein the grating is implemented in between the lens unit and the image detector.

* * * * *